US005460180A

United States Patent [19]
Klepper et al.

[11] Patent Number: 5,460,180

[45] Date of Patent: Oct. 24, 1995

[54] CONNECTION ARRANGEMENT AND METHOD OF OPERATION OF A 2D ARRAY FOR PHASE ABERRATION CORRECTION

[75] Inventors: John R. Klepper, Seattle; Levin F. Nock, Issaquah, both of Wash.

[73] Assignee: Siemens Medical Systems, Inc., Iselin, N.J.

[21] Appl. No.: 316,603

[22] Filed: Sep. 30, 1994

[51] Int. Cl.[6] .................... A61B 8/00

[52] U.S. Cl. .................... 128/661.01; 73/626

[58] Field of Search .................... 128/660.08, 661.01, 128/662.03; 73/620, 625, 626

[56] References Cited

U.S. PATENT DOCUMENTS

| | | | |
|---|---|---|---|
| 4,813,279 | 3/1989 | Shirasaka | 73/626 |
| 4,852,577 | 8/1989 | Smith et al. | 128/660.07 |
| 5,172,343 | 12/1992 | O'Donnell | 367/7 |
| 5,271,403 | 12/1993 | Paulos | 128/660.07 |
| 5,303,591 | 4/1994 | Dykes et al. | 73/620 |

OTHER PUBLICATIONS

"Aberration Correction on a Two-Dimensional Anisotropic Phased Array", O'Donnell et al., 1991 Ultrasonics Symposium, pp. 1189–1193.

"A Comparative Evaluation of Several Algorithms for Phase Aberration Correction", Ng et al., Submitted to IEEE UFFC Jul. 1993.

"An Evaluation of Transducer Design and Algorithm Performance for Two Dimensional Phase Aberration Correction", Trahey et al., 1991 Ultrasonics Symposium, pp. 1181–1187.

*Primary Examiner*—George Manuel

[57] ABSTRACT

An ultrasound imaging system of the type including a 2D transducer array which has first and second types of transducer elements. Each element of the first type occupies an area of the array which is an integral fraction of the area occupied by each element of the second type. A connection arrangement comprising a plurality of multiplexer/summation circuits is provided for electrically connecting the array elements to the remainder of the ultrasound imaging system. Each multiplexer/summation circuit has a plurality of signal inputs individually connected to a respective plurality of the elements of the first type for selectively combining a given number of the elements of the first type together, the given number being an inverse of the integral fraction. In a preferred embodiment of the invention the 2D array is generally rectangular in shape and has elements arranged into rows along its lateral dimension and columns along its elevational dimension, with a first lateral portion of the array including at least one column of elements of the first type and a second lateral portion of the array including columns of elements of the second type. The multiplexer/summation circuit has signal inputs connected individually to each of the elements of a column of the elements of the first type, for selecting the given number of elements to be combined.

4 Claims, 6 Drawing Sheets

CONNECTION ARRANGEMENT AND METHOD OF OPERATION OF A 2D ARRAY FOR PHASE ABERRATION CORRECTION

CROSS-REFERENCE TO RELATED APPLICATION

This application is related to an application entitled "A 2D Array For Phase Aberration Correction", filed by the present inventors simultaneously with the present application and assigned to the same assignee.

BACKGROUND OF THE INVENTION

1. Field of the Invention

The present invention relates to improvements in ultrasonic imaging, and more particularly, to a novel connection arrangement and method of operation of a 2D array which improves the performance of phase aberration correction processing while minimizing increases in circuit and processor complexity. The array includes first and second portions which are segmented into differently dimensioned elements in their elevation direction, wherein the first portion of the array is segmented into coarse elements and the second portion is segmented into fine elements. The connection arrangement selectively connects a plurality of the fine elements together so that the area of the 2D array corresponding to the connected fine elements is substantially the same size as the area of a coarse element.

2. Description of the Prior Art

Ultrasonic imaging has been extensively applied in virtually every medical specialty in the form of pulse-echo (B-mode) imaging. B-mode imaging systems display echoes returning to an ultrasonic transducer as brightness levels proportional to the echo amplitude. The display of brightness levels results in cross-sectional images of an object in a plane perpendicular to the transducer.

Current ultrasonic transducer arrays typically include transmit mode focusing and receive mode dynamic focusing, achieved by appropriate timing of the transmit signals and appropriate delaying of the received echoes. For example, a linear phased array consists of a single group of transducer elements arranged in a line which are operated to not only focus but also steer (angle) transmit and receive beams by appropriate timing of the transmit signals and the receive echoes.

Conventionally, the timing or phasing data is determined by assuming propagation of the ultrasound pulses through a homogeneous tissue medium with a uniform velocity of sound, usually 1540 m/sec.

The assumption of a constant velocity of sound in the body is also the design basis of all ultrasound scanning systems for converting round trip pulse-echo time of flight data into images. Unfortunately, this simple model for all human tissue is erroneous. The body is actually composed of a plurality of inhomogeneous layers of different tissues (fat, muscle and bone) with bumps and ridges of varying thicknesses and shapes, and therefore different acoustic velocities. These layers are situated between the transducer and, for example, an internal organ of interest. The propagation velocity of ultrasound varies from approximately 1470 m/see in fat to greater than 1600 m/sec in muscle and in nervous tissue, and to as much as 3700 m/sec in bone. If an incorrect average velocity is chosen, B-scan images (as well as other ultrasonic images, such as color flow images based on Doppler processing) develop image range and scan registration errors.

Under the assumption of a uniform tissue medium having constant sound propagation velocity, the presence of inhomogeneous tissues can result in image artifacts, range shifts, geometric distortions, etc. which degrade the ideal diffraction-limited lateral resolution, and increase the side lobes (which reduces the signal-to-noise ratio in the image).

These adverse effects of inhomogeneous and nonuniform tissue layers result in unknown phase aberrations associated with the inhomogeneities introduced across the transducer aperture. Many attempts have been made to overcome these aberrations using various signal processing techniques, generally referred to herein as phase aberration correction (PAC) processing.

PAC methods rely on comparison of the signal from one element or group of elements of an array (a correction element or group) to the signal received from another part of the array (a reference element or group), to develop a time delay for beamforming, of the correction group or element and the reference group. This time delay is optimized by any one of several methods, such as cross-correlation or speckle brightness. Such techniques are the subject matter of, for example, U.S. Pat. No. 4,852,577 (illustrative of investigations performed by Trahey et al. at Duke University) and U.S. Pat. No. 5,172,343 (illustrative of investigations performed by O'Donnell at General Electric), both incorporated herein by reference, to mention just two known PAC methods for ultrasound imaging systems.

After optimization, the value of the time delay for the correction element is fixed and then becomes part of the next reference group for optimizing a next correction element or group which is typically adjacent to the new reference group. The goal is to provide small adjustments in the time delay (the adjustments typically referred to as the "phase aberration correction profile") to correct for the defocusing effect of the forenoted tissue inhomogeneities.

Most array type ultrasound imagers use a 1-dimensional segmentation of the array (1D array) in the lateral dimension corresponding to the plane of the image. For good imaging performance, the elements are small and finely spaced in the lateral dimension (approx. 1 wavelength or less), however, the elevation (out of plane) dimension is fixed at a relatively large dimension (15 to 20 wavelengths, for example). This provides a fixed focal arrangement in the elevation dimension which defines the slice thickness of the planar image that is made.

As previously described, when the ultrasound signal propagates through an inhomogeneous medium such as the human body, variations in the index of refraction of the various tissues produce distortions of the wavefronts in both the lateral and elevational dimensions. The PAC process attempts to correct for such distortions in order to improve image quality, particularly contrast resolution. With a 1D array, it is obvious that the PAC process can only correct for distortions produced in the lateral dimension.

The effect of distortion in the elevation dimension is to produce a phase cancellation (destructive interference) caused by the phase sensitive integration of the signal over the elevation dimension of the array elements. This phase cancellation produces an unwanted amplitude modulation of the signal which produces speckle in the image, and can corrupt the reference group signal used for time delay optimization in a PAC algorithm. One approach used to compensate for this effect is to set a threshold on the correlation coefficient (or other similar figure of merit representative of the parameter being optimized in the PAC algorithm) between the reference group and the correction element or group, below which the time delay value is interpolated for that correction group or element between its nearest neighbors whose correlation coefficients have passed the threshold criteria. However, this only works well if the nearest neighbors have passed the threshold. If there are only a few, isolated threshold failures, this works fine; but if there are contiguous failures, then there is no good way to ensure accurate interpolation.

An alternative approach to improve the performance in the elevation dimension would be to construct a 2D array which segments the elements of the array in the elevation dimension as well as in the lateral dimension. See, for example, the paper by O'Donnell et al., entitled "Aberration Correction on a 2-Dimensional Anisotropic Phased Array" published in ULTRASONICS SYMPOSIUM 1991, pages 1189–1193, which discloses one type of array segmentation pattern in the elevation dimension which is used uniformly across the lateral dimension of a 2D array. The 2D array disclosed therein comprises a symmetric arrangement of rows of elements, the rows having varying height and less elements per row as the distance of the row from the center of the array increases in the elevation dimension. Due to the changing height of the rows and the changing number of elements per row, such an array would be difficult to construct and would require many signal processing channels. Furthermore, an element from one row will have a given specific acoustic impedance (the specific acoustic impedance being a function of the mechanical impedance per unit area of the element, being directly proportional to the electrical source impedance of the element, and determining the amplitude and frequency response of the element). However, an element from a row of different height will have a different specific acoustic impedance. Therefore the specific acoustic impedance of any particular element will depend on its surface area. Since for ideal beamforming and for PAC, the specific acoustic impedance of all elements should be identical, the O'Donnell array is somewhat undesirable.

Ideally, to achieve best results for PAC, the segmentation in the elevation dimension should be as fine as in the lateral dimension. However, since each element requires its own channel of electronics, such an arrangement would be difficult to build and could require many pulse repetition periods (PRP's) in order to perform a PAC algorithm. This makes the image frame rate very slow. With such a slow frame rate, if there is any motion in the field of view or movement of the transducer, the PAC results will be degraded, unless the motion is taken into account (by, e.g., starting the PAC algorithm over again). Therefore, there is some trade-off between the number of array elements and the results of the PAC processing. A paper entitled "A Comparative Evaluation of Several Algorithms for Phase Aberration Correction" by Ng et al of Duke University, published in the September 1994 issue of the IEEE Transactions on Ultrasonics, Ferroelectrics, and Frequency Control, Vol. 41, No.5, pp. 631–643, acknowledges that the fundamental problem of all current PAC techniques is the low correlation between the elements of adjacent rows. Ng et al vaguely states that some edge geometries are being investigated to reduce the center-to-center elevational distance at the edges of the array, however no specific arrangements are disclosed and it is specifically stated that providing elements which are divided more finely in the elevation dimension (such as in the forenoted O'Donnell paper) is undesirable because of the corresponding increase in the complexity of the array, the difficulty of its manufacture, and the complexity of the hardware needed to control it.

With the ever increasing desire for larger size and higher resolution images, 2D arrays are finding increased use, and in particular 2D arrays which have fine elements in the elevation dimension, in order to improve the performance of PAC processing. Due to the increase in the number of elements of the array, there is a corresponding increase in the complexity of the required signal processing circuitry. It is an object of the present invention to provide a connection arrangement for a 2D array which is relatively simple to construct and at the same time does not appreciably limit the flexibility of the remainder of the signal processing circuitry.

SUMMARY OF THE INVENTION

In accordance with the principles of the present invention, for use in an ultrasound imaging system a 2D transducer array is provided which has first and second types of transducer elements. Each element of the first type occupies an area of the array which is an integral fraction of the area occupied by each element of the second type. A connection arrangement is provided for connecting the array elements to the remainder of the ultrasound imaging system, which connection arrangement comprises a plurality of multiplexer/summation circuits. Each multiplexer/summation circuit has a plurality of individual input signal connections connected individually to a corresponding plurality of the elements of the first type for selectively combining a given number of the elements of the first type together, the given number being an inverse of the integral fraction. In a preferred embodiment of the invention the 2D array is generally rectangular in shape and has elements arranged into rows along its lateral dimension and columns along its elevational dimension, with a first lateral portion of the array including at least one column of elements of the first type and a second lateral portion of the array including columns of elements of the second type. The multiplexer/summation circuit has signal inputs connected individually to each element of a column of the elements of the first type, for selecting the given number of elements to be combined.

In accordance with a further aspect of the invention, the output impedance of the multiplexer/summation circuit matches the input impedance of the remainder of the ultrasound imaging system These and other objects and advantages of the invention will be apparent from the following description of the preferred embodiments, and from the claims. For a fuller understanding of the present invention, reference should now be made to the following detailed description of the preferred embodiments of the invention and the accompanying drawings.

DETAILED DESCRIPTION OF THE PREFERRED EMBODIMENTS

Figure 1:
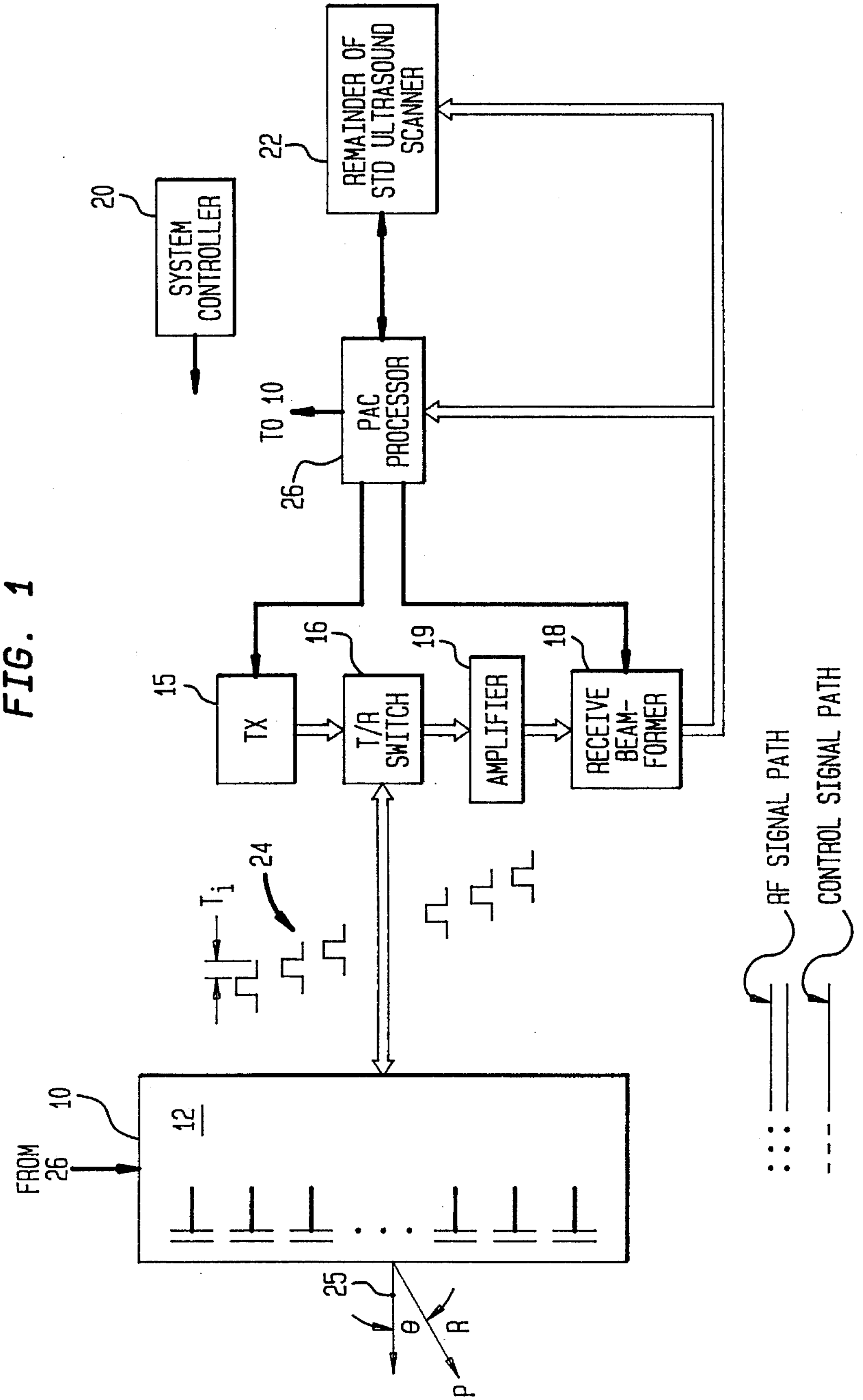
FIG. 1 illustrates in a simplified block diagram form an ultrasound imaging apparatus in which the present invention is useful.

Referring now to FIG. 1, a vibratory energy (e.g., ultrasound) imaging system includes a probe 10 having a transducer array 12 comprised of a plurality of separately driven elements 14 which each produce a burst of vibratory energy, such as ultrasonic energy, when energized by a pulse produced by transmit circuitry (TX) 15. The energizing pulses are applied to elements 14 via a set of transmit/receive (T/R) switches 16, electrical signal conductors in a transducer cable 17, and electrical connections not specifically shown in probe 10 (but shown, e.g., in FIGS. 4*a* and 4*b*). The vibratory energy reflected back to transducer array 12 from the subject under study is converted to an electrical signal by each transducer element 14 and applied separately to a receive beamformer (RCVR) 18 through transmit/receive (T/R) switches 16 and individual amplification stages 19. Each channel of the amplification stages 19 include an input matching impedance, followed by a low noise pre-amplifier and finally by a variable gain stage used for a portion of a user controlled time/gain compensation, commonly referred to as TGC, as is conventional in the art. Transmit circuitry 15, beamformer 18, T/R switches 16 and amplification stages 19 are operated under control of a system controller 20 which is responsive to commands by a human operator for proper operation of the imaging system. A complete image scan is performed by acquiring a series of echoes in which switches 16 are initially set to their transmit position, and transmit circuit 15 is activated so as to provide a series of pulse signals to selectively energize each transducer element 14. Thereafter, T/R switches 16 are set to their receive position, and the subsequent echo signals produced by each transducer element 14 in response to impingement thereon of reflected ultrasound energy are applied, via the individual channels of the amplification stages 19, to the receive beamformer 18. In receive beamformer 18 the separate echo signals from each transducer element 14 are digitized, appropriately delayed relative to one another, and combined to produce a single echo ("beam") signal which is then detected and scan converted to produce each line in an image displayed on a display included in the remainder portion of an echo imaging system 22, such as is conventional in ultrasound imaging systems.

As well known in ultrasound imaging systems, transmit circuitry 15 drives transducer array 12 such that the ultrasonic energy produced, is directed, or steered, in a beam. A B-scan can therefore be performed by moving this beam through a set of angles from point-to-point rather than physically moving transducer array 12. To accomplish this, transmit circuitry 15 imparts a time delay ($T_i$) to the respective pulses 24 that are applied to successive transducer elements I 14. If the time delay is zero ($T_i$=0), all of transducer elements 14 are energized simultaneously and the resulting ultrasonic beam is directed along an axis 25 which is normal to the transducer face and originating from its center. If the time delay ($T_i$) increases as a function of element number I, then the ultrasonic beam is directed downward from central axis 25 by an angle Θ, e.g., as illustrated in FIG. 1. The relationship between the time delay increments $T_i$ and the resulting beam steering is well known and conventional in ultrasound imaging, and therefore further description of beam steering will be omitted.

Referring still to FIG. 1, the echo signals (reflections) produced by each burst of ultrasonic energy emanate from reflecting objects (reflectors) located at successive positions along the ultrasonic beam. These are sensed separately by each element 14 of transducer array 12 and a sample of the magnitude of the echo signal at a particular point in time represents the amount of reflection occurring at a specific range (R). Due to differences in the propagation paths between a focal point P and each transducer element 14, however, these echo signals will not occur simultaneously, and their amplitudes will not be equal. The function of receive beamformer 18, as well known, is to impart an appropriate time delay to each echo signal and sum them together so as to provide a single echo signal which accurately indicates the total ultrasonic energy reflected from each focal point P located at range R along the ultrasonic beam oriented at the angle Θ. A combination of the echo signals to generate an image results in the formation of an image representative of the shape of the reflectors, as well known.

To simultaneously sum the electrical signals produced by the echoes from each transducer element 14, system controller 20 controls the transmit circuit 15 and beamformer 18 so that time delays are introduced into each separate transducer element channel of beamformer 18. In the case of linear array 12, the delay introduced in each channel may be divided into two components; one component is the beam steering time delay, and the other component is the beam focusing time delay. The beam steering and beam focusing time delays are precisely the same delays ($T_i$) as the transmission delays described above. However, the focusing time delay component introduced into each receiver channel is continuously changing during reception of the echoes to provide dynamic focusing of the received beam at the range R from which the echo signal emanates. Dynamic focusing is also well known and its further description is therefore omitted.

As well known, under direction of system controller 20, beamformer 18 introduces delays to the signals received during the scan such that steering of beamformer 18 tracks with the direction (Θ) of the beam steered by transmit circuit 15, and it samples the echo signals at a succession of ranges (R) and provides the appropriate delays to dynamically focus at points P along the beam. Thus, each emission of an ultrasonic pulse results in reception of a series of echo signal samples which represent the amount of reflected sound from a corresponding series of points P located along the ultrasonic beam. Receive beamformer 18 is able to rapidly change its delays for each echo signal sample to dynamically focus on the reflectors which produce the signal sample. The stream of focused and steered echo signal samples which are produced by the receive beamformer 18 are referred to as the "received beam".

It must be appreciated, however, that the time delays produced to provide the desired steering and focusing during both the transmit mode and receive mode presume that the sound wave travels through the body at a uniform velocity. However, as previously noted, in clinical applications this is usually not the case. Instead, the ultrasonic energy typically passes through one or more layers of tissue which have different sound propagation characteristics. A boundary between such layers typically has an irregular shape. As a result, for example, when beam samples are being acquired from a point P at a steering angle Θ, sound traveling between point P and two separate array elements is propagated quite differently due to the irregularity of the boundary. This results in a difference in ultrasound path length between the point P and the two array elements which is not determined solely by the geometric relationship between the point and the array elements. This difference in path length based on the different propagation characteristics of the intervening tissues causes the phase errors for which the PAC processing techniques are directed.

The corrections for phase errors caused by the aberrations in the sound propagating tissue are different for each transducer element 14 and for each steering angle Θ acquired during the scan. Typically, during a PAC "adaptive mode" of the imager, the beam signals from the received beamformer 18 are not used for forming an image and instead are applied to a PAC processor 26 which implements one of several known PAC algorithms, such as those noted in the U.S. Patents referred to in the Background portion of the specification, to calculate the phase corrections (PAC profile) required to be provided to the signals associated with each transducer element 14 in order to offset the above-noted sound propagating errors. Then, during an "imaging mode" of the imager, these calculated corrections are applied, as well known, to augment the time delays normally calculated by system controller 20 for the transmit circuit 15 and receive beamformer 18 which would not have taken PAC into account. The result is that the combined, augmented, time delays effect a reduction of the image distortions caused by phase aberrations.

It is noted that ultrasound machines typically include a mid-processor section which follows the receive beamformer 18, and includes an echo processor and a flow processor. The echo processor processes the amplitude of the received beams for generating signals which are applied for displaying the known and conventional B-mode and M-mode images. The flow processor is principally used for processing the received beams for generating signals which are applied for displaying the known and conventional colorflow images. In the preferred embodiment, the flow processor carries out an auto-correlation type of signal processing (well know to those of ordinary skill in the art), which can conveniently be time-multiplexed (i.e., between the PAC adaptive/imaging modes of the imager), so as to carry out a cross-correlation type of PAC processing of the received echo signals. Thus, with simple modification, a conventional flow processor can comprise PAC processor 26.

As previously noted, it is desirable to calculate PAC correction values in the elevation dimension as well as in the lateral dimension, due to unwanted amplitude modulation of the image signal which produces speckle in the image and can corrupt the signal used as the reference group in the PAC algorithm. A known approach to improve the performance in the elevation dimension would be to construct a 2D array which segments the elements of the array in the elevation dimension as well as the lateral dimension. See, for example, the forenoted paper by O'Donnell et al., entitled "Aberration Correction on a 2Dimensional Anisotropic Phased Array". Ideally, to achieve best results for PAC, the segmentation in the elevation dimension should be as fine as in the lateral dimension. However, since each element requires its own channel of electronics, such an arrangement would be difficult to build and could require many pulse repetition periods (PRP's) in order to perform a PAC algorithm, depending on how PAC is implemented. This makes the image frame rate very slow. With such a slow frame rate, if there is any motion in the field of view or movement of the transducer, the PAC results will be degraded, unless the motion is taken into account by, e.g., recalculating the PAC profile. Therefore, there is some trade-off between the number of array elements and the result of the PAC processing.

Figure 2A:
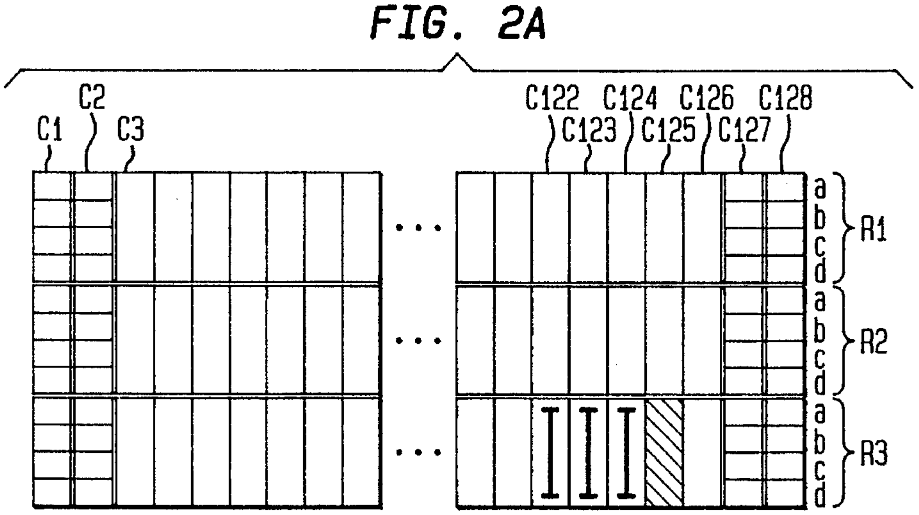
FIGS. 2*a* to 2*o* illustrate a 2D array for which the connection arrangement of the present invention is particularly useful, for use in the ultrasound imaging apparatus shown in FIG. 1, as well as one example for the stepping of a PAC algorithm correction window through the array.
Figure 2B:
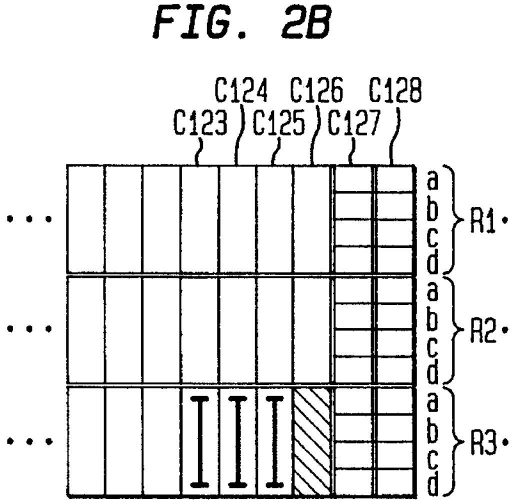
Figure 2C:
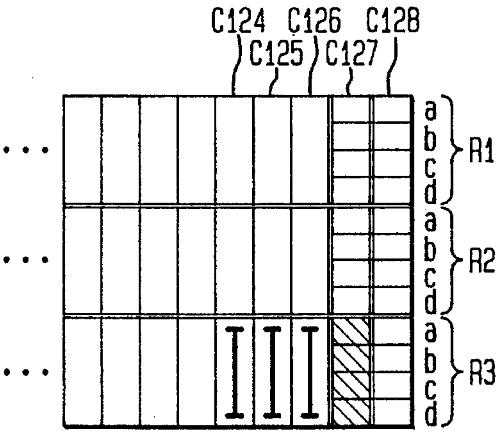
Figure 2D:
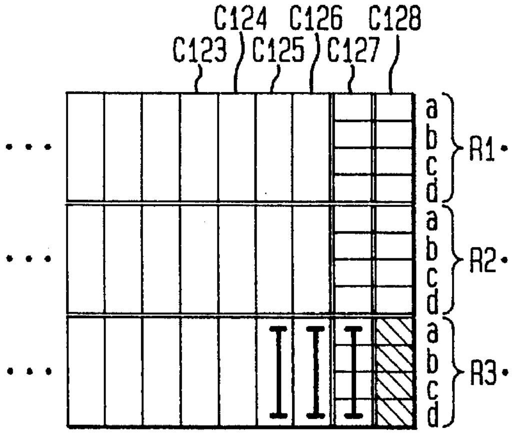
Figure 2E:
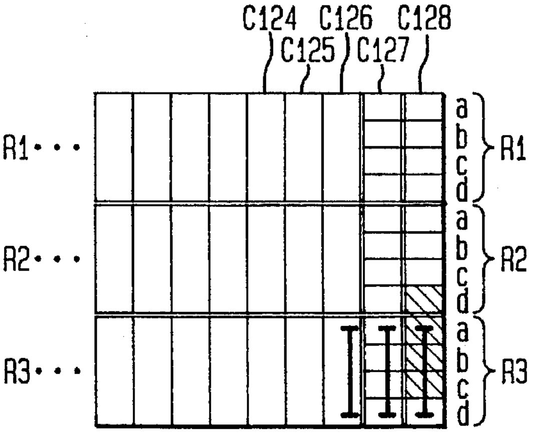
Figure 2F:
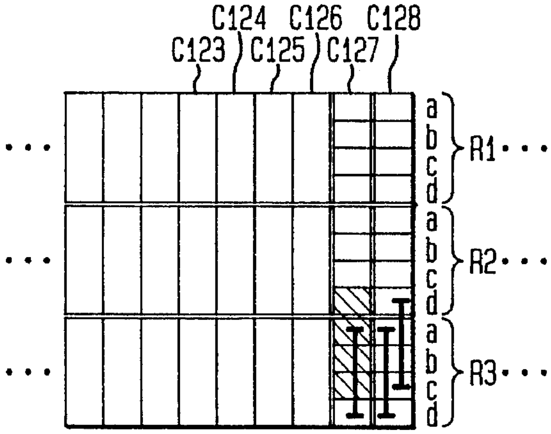
Figure 2G:
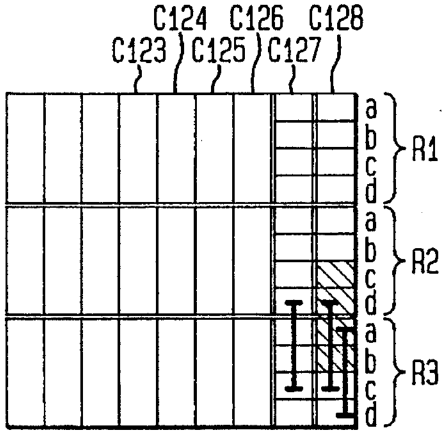
Figure 2H:
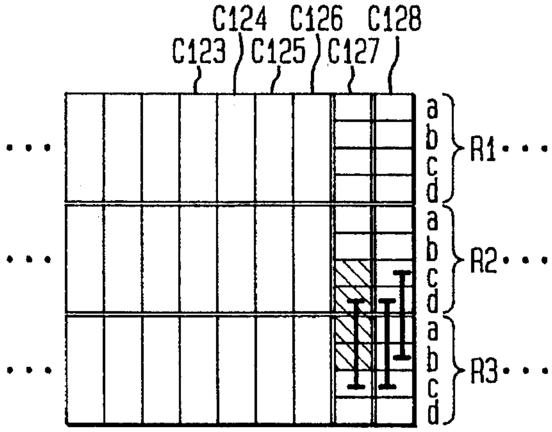
Figure 2I:
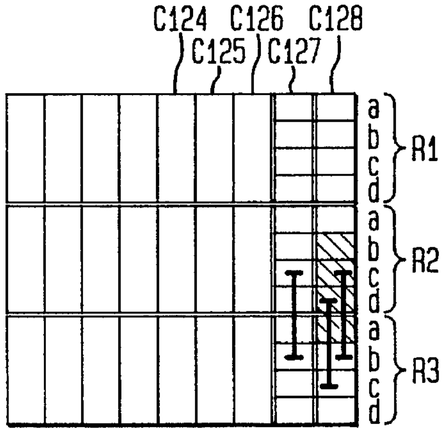
Figure 2J:
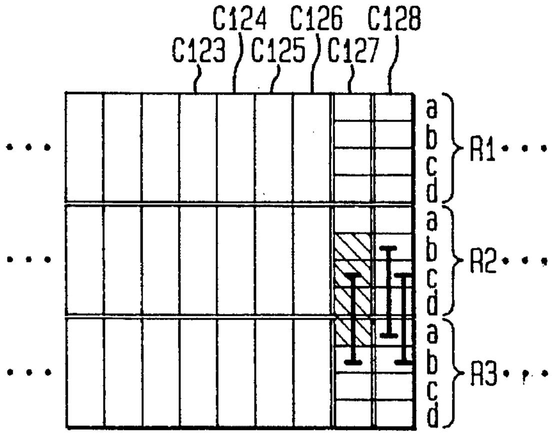
Figure 2K:
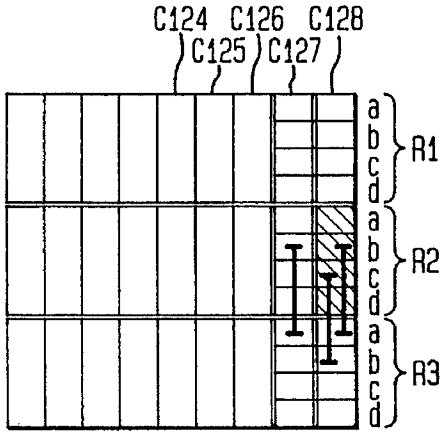
Figure 2L:
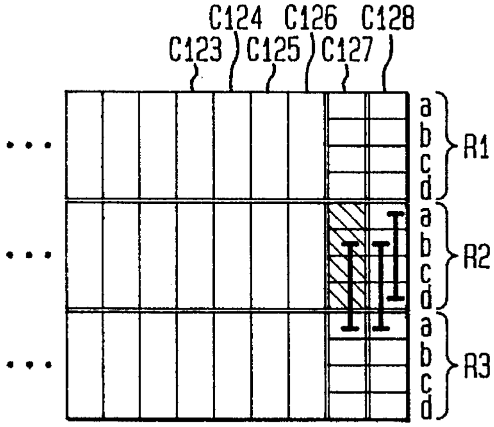
Figure 2M:
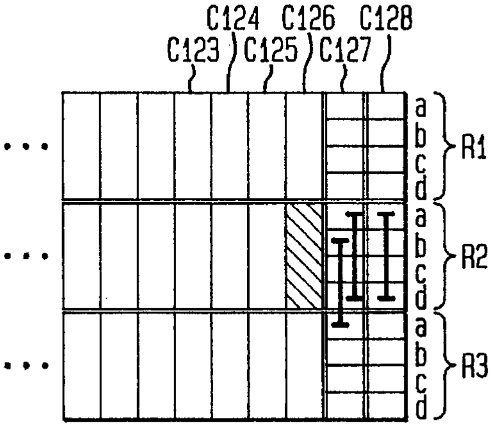
Figure 2N:
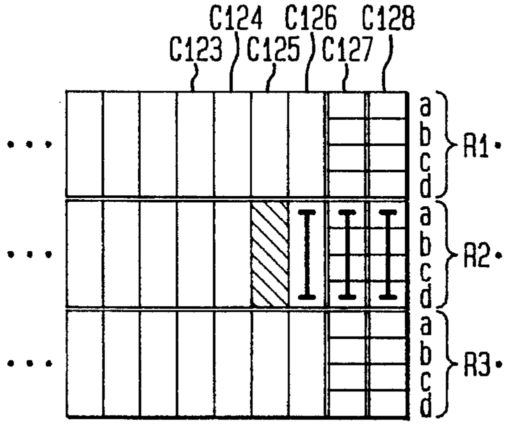
Figure 2O:
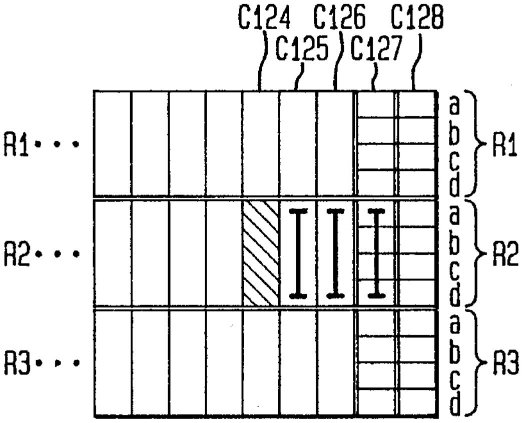

FIGS. 2*a* to 2*o* illustrate one example of a 2D array constructed in accordance with the principles of the present invention for use in the ultrasound imaging apparatus shown in FIG. 1, as well as a stepping of a PAC algorithm correction window through the array. In accordance with one aspect of the invention, a central portion of transducer array 12 is coarsely segmented in the elevation dimension and the lateral end segments are finely segmented. In the illustrated embodiment, array 12 has 3 rows (R1, R2 and R3) and 128 columns (C1 to C128), where the columns in a central portion (C3–C126) include one course element per row. The columns in the end segments (C1, C2 and C127, C128) have four elements each (a, b, c, and d) in the elevation direction in each row. It is noted that other similar configurations, such as one with 5 rows, and having course elements in the central portion, and at least 1 column at each lateral end with its rows divided into several additional elements each, would work just as well.

A primary feature of the novel 2D array is the provision of one or more columns of fine elements. Since the fine elements are arranged in columns, construction of the array is a relatively simple task. That is, columnar sections having fine elements and coarse elements are constructed separately and then glued together in the desired configuration, such as shown in FIG. *2a*, *3a* or *3b*. An additional advantage of the novel 2D array is that, depending upon the electronics connecting the array elements to the beamformer, the fine elements can be used for beamforming in the elevation dimension.

Due to the use of both coarse and fine elements, consideration should be given to matching both the specific acoustic impedance and electrical impedance of these elements. In accordance with the invention, signal from several (e.g., 4) of the fine elements are selectively combined so as that the combined fine elements present substantially the same electrical source impedance to the remainder of the ultrasound imaging apparatus as that presented by each of the coarse elements, in order to maintain the signal uniformity necessary for accurate PAC calculation as well as high quality imaging. As will be described in detail later on with respect to FIG. *4a*, the signal from the fine elements are combined by multiplex/summation (MUX/sum) chip circuits located in probe 10.

In general, PAC and/or elevational steering will perform better when there is a large number of columns with finely-spaced elements. On the other hand, a smaller number of these columns will decrease the complexity and cost of the transducer and associated electronics. Thus, each particular system will involve a compromise between performance and cost.

For the presently disclosed 2D array, the PAC operation is performed by forming a signal from an initial reference group of elements of the array and using that signal as a basis to correct an adjacent element or group of elements. The corrected element or group is then included in the reference group, and the most distant element of the reference group is excluded. This stepping is conceptually similar to a spatial boxcar or sliding window averager.

In the following example, illustrated by FIGS. 2*a* to 2*o*, the initial reference group is taken to be 3 elements in one row (R3) and the correction element is the adjacent element to the right. FIG. 2*a* illustrates the Ith iteration on the bottom row (R3) as a PAC algorithm correction window steps toward the right-hand end of array 12. On succeeding PRP's, illustrated by FIGS. 2*b* to 2*o* (which show only the right-hand end of array 12 for simplicity), the correction window proceeds step wise to the end of the array by moving the correction window from row R3 to row R2, and then proceeds along array 12 in a serpentine fashion from row R2 to row R1, where the correction window finally reaches the opposite end of the array. The particular type of PAC correction algorithm used is not important for understanding the present invention, and any one of several well known algorithms could be used. Furthermore, more or fewer elements could be used in the reference group.

More specifically, as shown in FIG. 2*b*, the reference group of elements has stepped one element to the right (from columns C122–C124 to C123–C125) and the correction element is in column C126. FIG. 2*c* shows the reference group stepped one more column to the right (now columns C124–126) so that it is adjacent a correction element comprising a group of four fine elements (elements R3*a*–R3*d* of column C127).

Figure 4A:
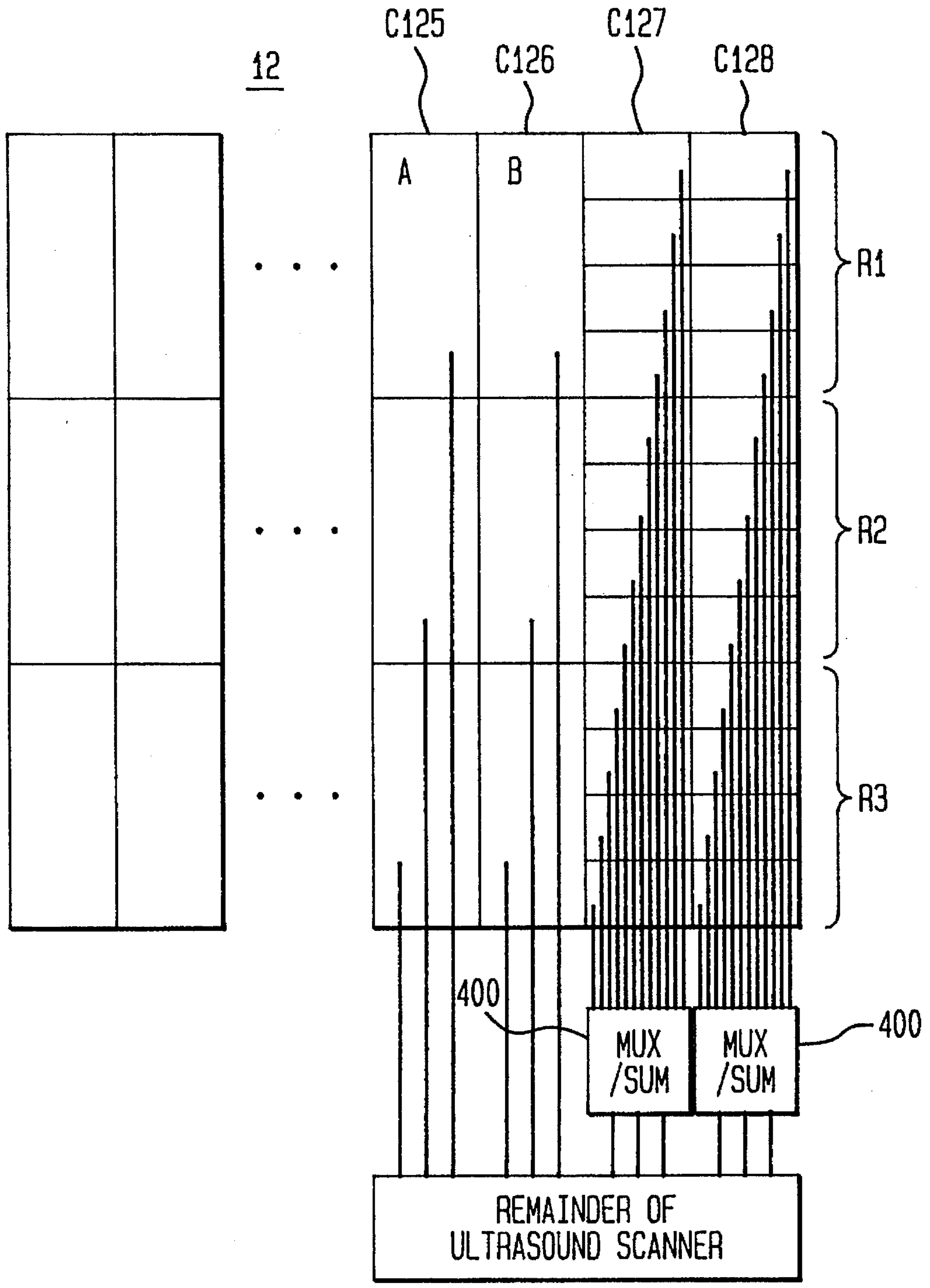
FIG. 4*a* illustrates a connection arrangement constructed in accordance with the principles of the present invention for use to connect the transducer of FIGS. 2 or 3 to the remainder of the ultrasound scanner.

The signals from these four elements are summed in a Mux/sum chip 400, shown in FIG. 4*a*. The output from Mux/sum chip 400 is attached to a single Tx/Rx channel of the scanner, so that the four fine elements appear as one coarse (regular-sized) element to the scanner. The output impedance of the Mux/sum chip is designed to match the impedance of the transducer cable 17. This maintains a uniformity in the impedance presented to beamformer 18 during the PAC processing, previously noted as being an important aspect achieved by the present invention.

FIG. 2*d* illustrates a further stepping of the reference group one more column to the right so that the correction group now comprises elements R3*a*–R3*d* of column 128. FIG. 2*e* illustrates the reference group as including the elements in row R3 for columns C126, C127 and C128, while the correction group of elements comprises elements R2*d* through R3*c* of column C128 apparatus.

As shown in FIGS. 2*f*–*fo*, the reference and correction groups move stepwise from row R3 to R2 until a combining of the fine elements into a group is no longer needed, i.e., after FIG. 20.

Applicants novel design and connection arrangement therefore allows the transition from row to row to be made on a gradual basis, thereby maintaining a high degree of correlation between the echo signals during this process. Without this, the center to center distance between rows is so great that the correlation coefficient between the signal from the reference group in one row and the correction group in the next row may be so small that the accuracy of the phase aberration correction may be lost and the whole operation becomes meaningless. Unlike the case for 1D arrays, where values with poor correlation can be interpolated, the probability of being able to reliably do such an interpolation in the elevation direction for a 2D array is relatively low.

It is noted that FIG. 2 represents one preferred embodiment of this invention. There are many other possible combinations of reference groups and correction groups which can be connected in various sequences or, with sufficient hardware, in parallel. Furthermore, the present invention is beneficial when making row-to-row transitions, regardless of the particular sequence of reference groups and correction groups chosen.

Figure 3A:
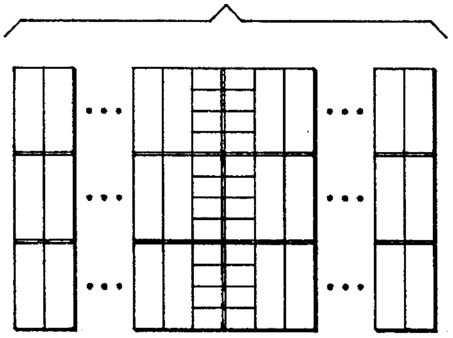
FIGS. 3*a* and 3*b* illustrate alternative embodiments of a transducer array useful in the ultrasound imaging apparatus shown in FIG. 1.

FIG. 3*a* illustrates an alternative configuration of a 2D transducer useful with a connection arrangement constructed in accordance with the principles of the invention, which is basically equivalent in operation and function to that shown in FIG. 2, and is an array with one (or preferably two) columns of the fine elements positioned in the center of the array, and with columns of the coarse elements positioned at either side. Although this approach may be more difficult to build, it has the advantage that the PAC processing could begin in the center of the array and move outward towards both of its edges, thereby minimizing the accumulated phase jitter because of the shorter distance over which the PAC algorithm is performed (since the rows are "tied together" in the center). Furthermore, it is noted that with a larger number of columns of fine elements in the center( e.g., 16 or 32), this array configuration would also allow steering of the ultrasound beams in the elevation direction, and may therefore be particularly useful, e.g., when imaging a biopsy probe. Note, however, that in order to perform this "fine element" elevational steering, the signal connections from the fine elements to the beamformer must consist of individual receive channels, rather than a grouping of the fine elements as is done in the illustrated FIG. 4 embodiment using MUX/sum chip 400, and the summing of the fine channels takes place in the beamformer.

Figure 3B:
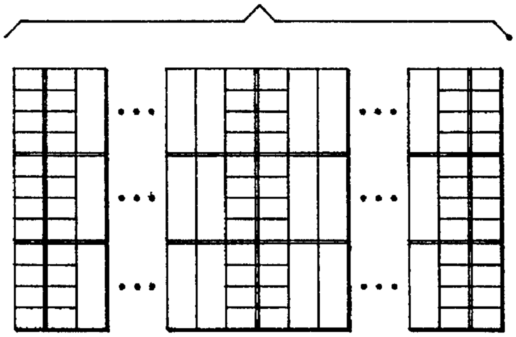

FIG. 3*b* illustrates a further alternative configuration which is a combination of the two above-described configurations and has columns of fine elements at the center as well as at both lateral ends of the array. This would allow iterative fine corrections between the rows of elements and also allow the PAC processing to be performed in a "loop" configuration. The loop configuration allows the property of "phase closure" to be used as a confirmation of accurate PAC processing. An additional advantage of this embodiment is that the plurality of opportunities to perform phase closure results in a more "area specific "PAC" processing, which has specific advantageous in the event of patient and/or probe motion which does not effect the entire area being imaged.

FIG. 4*a* illustrates the novel circuit arrangement constructed in accordance with the principles of the present invention for connecting the transducer of FIG. 2 (or 3) to the remainder of the ultrasound scanner in a simple manner which is compatible with the degree of transducer element access required for PAC processing in accordance with the invention and, with only a minimal increase in circuit complexity. The illustrated embodiment uses two Multiplex/Sum stages (MUX/Sum) 400 for optimizing the specific acoustic impedance presented by a given number (4) of the fine elements (B in columns C127 and C128), which are combined so as to match the specific acoustic impedance presented by each coarse element. The specific acoustic impedance of the combined fine elements matches that presented by each coarse element because the total area of piezoelectric crystal used for a coarse element A is the same area as that used for 4 of the fine elements B. Thus, the area of a fine element is an integral fraction of the area of a coarse element. MUX/Sum stages 400 could be constructed as an ASIC and located in the transducer handle, or as a circuit in the ultrasound scanner itself. The MUX/Sum output connection presents the same electrical source impedance to the remainder of the ultrasound scanner as that provided by a direct connection to a coarse element (A). Inside the MUX/Sum block, signals from several fine elements B (4 elements, in this example) are summed together to form the output.

Although the illustrated embodiment is somewhat limiting with respect to beamsteering in the elevation direction, i.e., only coarse element steering), a significant advantage of the invention is the reduced signal connection complexity which it provides.

Figure 4B:
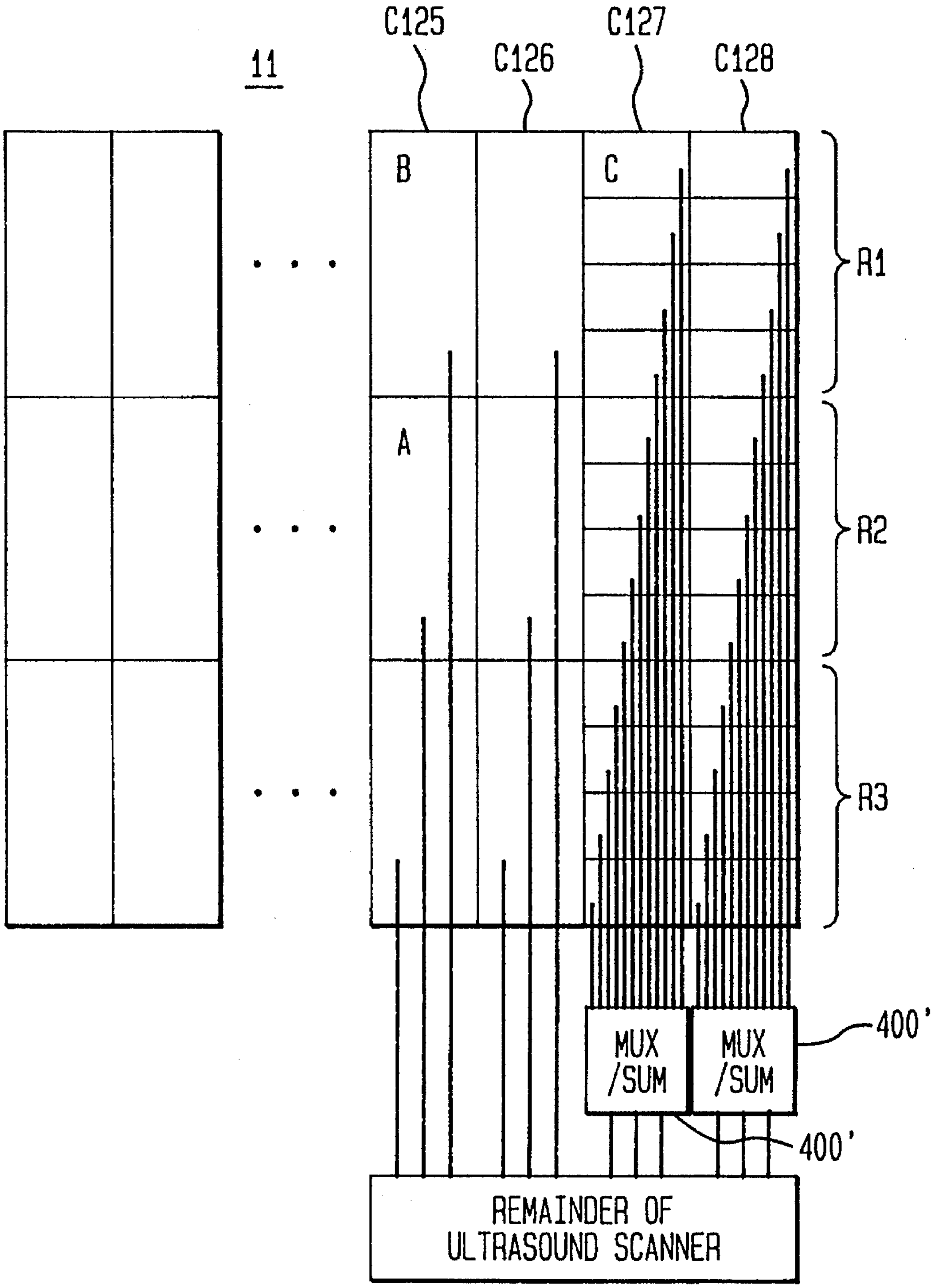
FIG. 4*b* illustrates an alternative embodiment of the FIG. 4*a* arrangement.

In this example, all of the coarse elements A are of equal size. However, for optimal elevational focus, unequally sized rows may be desirable. This possibility is illustrated in FIG. 4*b*, where the center row (R2) is larger. The MUX/Sum block illustrated herein is flexible, and can match coarse elements A or B by summing the appropriate number of fine elements in accordance with the principles of the invention, and described, for example, with reference to FIGS. 2*a*–2*o*.

Thus, there has been shown and described a novel 2D transducer array and method for operation therefore for adaptive phase aberration correction which satisfies all the objects and advantages sought therefore. Many changes, modifications, variations and other uses and applications of the subject invention will, however, become apparent to those skilled in the art after considering this specification and its accompanying drawings, which disclose preferred embodiments thereof. For example, more than two adjacent columns having the fine elements could be used at a given location, such as at the lateral ends and/or the center of the array. In fact, since phase aberration is a local phenomena, the columns of fine elements could be spaced uniformly across the lateral dimension of the array. In this embodiment, the structure of FIG. 3 could be modified, e.g., to have two columns of fine elements after each N columns of coarse elements. An additional advantage of this embodiment is that it significantly increases the opportunities to perform phase closure, thereby permitting an even more "area specific" PAC processing. Furthermore, other connection arrangements could be provided between the transducer array and the beamformer, such as the provision of preamplifier circuits in the probe for each fine element, and the fine element summation being carried out just before the beamformer. All such changes, modifications, variations and other uses and applications which do not depart from the spirit and scope of the invention are deemed to be covered by the invention which is limited only by the claims which follow.

We claim:

1. A vibratory energy imaging system, comprising:

a 2D transducer array having a plurality of transducer elements for generating pulses of vibratory energy which are directed towards reflectors and which receive reflections of said vibratory energy and develop echo signals in response thereto, said transducer array having first and second types of transducer elements, the first type occupying an area of the array which is an integral fraction of the area occupied by each element of the second type;

signal processing apparatus for processing said echo signals so as to produce an image signal representative of a shape of said reflectors;and a connection arrangement for connecting said elements to said signal processing apparatus, comprising at least one multiplexer/summation circuit having a plurality of signal inputs individually connected to a respective plurality of the elements of the first type for selectively combining a given number of the elements of the first type together, the given number being an inverse of the integral fraction.

2. The vibratory energy imaging system of claim 1, wherein:

the 2D array is generally rectangular in shape and has elements arranged into rows along its lateral dimension and into columns along its elevational dimension, with a first lateral portion of the array including at least two columns of a plurality of elements of the first type and a second lateral portion of the array including columns of a plurality of elements of the second type, with the second lateral portions being positioned adjacent the first lateral portions; and the connection arrangement including a plurality of multiplexer/summation circuits corresponding in number to the plurality of columns having elements of the first type, each multiplexer/summation circuit having signal inputs connected individually to each of the elements of the first type of a corresponding column and selecting the given number of elements to be combined.

3. The vibratory energy imaging system of claim 2, wherein:

the signal processing apparatus has a given input impedance; and the multiplexer/summation circuit has an output impedance which matches the given input impedance.

4. A method of operating a vibratory energy imaging system, comprising the steps of:

energizing a 2D transducer array having a plurality of transducer elements of first and second types of transducer elements, the first type occupying an area of the array which is an integral fraction of the area occupied by each element of the second type, and generating pulses of vibratory energy which are directed towards reflectors in response thereto;

receiving reflections of said vibratory energy at said 2D transducer array, with said elements developing electrical echo signals in response thereto; and connecting the electrical echo signals developed by each of said elements to a signal processing apparatus for developing an image signal representative of a shape of said reflectors, said connecting comprising individually connecting each of said elements of said second type directly to said signal processing apparatus, and connecting each of the elements of said first type to said signal processing apparatus via a multiplexer/summation circuit having a plurality of signal inputs individually connected to a respective plurality of the elements of the first type for selectively combining a given number of the elements of the first type together, the given number being an inverse of the integral fraction.

* * * * *